United States Patent
Etter

(10) Patent No.: US 10,130,636 B2
(45) Date of Patent: Nov. 20, 2018

(54) HIGH DOSAGE STRENGTH TABLETS OF RUCAPARIB

(71) Applicant: Clovis Oncology, Inc., Boulder, CO (US)

(72) Inventor: Jeffrey Etter, Boulder, CO (US)

(73) Assignee: Clovis Oncology, Inc., Boulder, CO (US)

( * ) Notice: Subject to any disclaimer, the term of this patent is extended or adjusted under 35 U.S.C. 154(b) by 0 days.

(21) Appl. No.: 15/920,643

(22) Filed: Mar. 14, 2018

(65) Prior Publication Data
US 2018/0200260 A1    Jul. 19, 2018

Related U.S. Application Data

(62) Division of application No. 14/828,065, filed on Aug. 17, 2015, now Pat. No. 9,987,285.

(60) Provisional application No. 62/040,849, filed on Aug. 22, 2014, provisional application No. 62/101,739, filed on Jan. 9, 2015.

(51) Int. Cl.
| | |
|---|---|
| *A61K 9/20* | (2006.01) |
| *A61K 31/55* | (2006.01) |
| *A61P 35/00* | (2006.01) |
| *A61K 31/185* | (2006.01) |

(52) U.S. Cl.
CPC ............ *A61K 31/55* (2013.01); *A61K 9/2009* (2013.01); *A61K 9/2054* (2013.01); *A61K 9/2059* (2013.01); *A61K 31/185* (2013.01); *A61P 35/00* (2018.01)

(58) Field of Classification Search
None
See application file for complete search history.

(56) References Cited

U.S. PATENT DOCUMENTS

| | | |
|---|---|---|
| 6,495,541 B1 | 12/2002 | Webber et al. |
| 6,977,298 B2 | 12/2005 | Webber et al. |
| 7,268,126 B2 | 9/2007 | Liu et al. |
| 7,323,562 B2 | 1/2008 | Ma et al. |
| 7,351,701 B2 | 4/2008 | Helleday et al. |
| 7,429,578 B2 | 9/2008 | Webber et al. |
| 7,531,530 B2 | 5/2009 | Helleday et al. |
| 8,754,072 B2 | 6/2014 | Basford et al. |
| 9,045,487 B2 | 6/2015 | Basford et al. |
| 9,987,285 B2 | 6/2018 | Etter |
| 2006/0074073 A1 | 4/2006 | Steinfeldt et al. |
| 2011/0136883 A1 | 6/2011 | Injac et al. |
| 2012/0302550 A1 | 11/2012 | Basford et al. |
| 2014/0044802 A1 | 2/2014 | Pollard et al. |
| 2015/0238504 A1 | 8/2015 | Basford et al. |
| 2016/0051561 A1 | 2/2016 | Etter et al. |

FOREIGN PATENT DOCUMENTS

| | | |
|---|---|---|
| WO | WO 2004/087713 A1 | 10/2004 |
| WO | WO 2011/098971 A1 | 8/2011 |
| WO | WO 2016/028689 A1 | 2/2016 |

OTHER PUBLICATIONS

Liu et al. (2014) "PARP inhibitors in ovarian cancer: Current status and future promise", Gynecologic Oncology 133:362-369.
Extended European Search Report issued in European Patent Application No. 15833096.9, dated Mar. 20, 2018, 8 pages.
Carnaby-Mann et al. (Nov. 2005) Arch Otolaryngol Head Neck Surg 131:970-975, "Pill Swallowing by Adults with Dysphagia".
Clinical Trials NCT01482715 "A study of oral Rucaparib in Patients with a solid tumor" Aug. 7, 2014.
Gillmore, et al. (Nov. 2012) Org. Process Res. & Dev., 16:1897-1904, "Multkilogram Scale-Up of a Reductive Alkylation Route to a Novel PARP Inhibitor".
International Preliminary Report on Patentability dated Feb. 28, 2017 in PCT/US2015/045522.
Kristeleit et al. 2013 ASCO Annual Meeting, poster, "A phase I dose-escalation and PK study of continuous oral rucaparib in patients with advanced solid tumors".
Kristeleit et al., A phase I dose-escalation and PK study of continuous oral rucaparib in patients with advanced solid tumors, 2013 ASCO Annual Meeting. J.Clin.Oncol., 2013, vol. 31, Supp., Abstract 2585.
Lachman et al. (1976). "The Theory and Practice of Industrial Pharmacy", Second edition. Chapter 11, Tablets, pp. 321-358. Philadelphia: Lea & Febiger.
Lachman et al. (1986) "The Theory and Practice of Industrial Pharmacy", Third edition. Chapter 11, Tablets, pp. 293-294. Philadelphia: Lea & Febiger.
Notice of Opposition and Arguments filed by Hamm & Wittkopp Patentanwalte PartmbB on Jun. 20, 2017 in EP2534153.
Notice of Opposition and Arguments filed by Hexal AG on Jun. 20, 2017 in EP2534153.
Overguard et al. (2001) Pharm World Sci 23(5):185-188, "Patient's evaluation of shape, size, and colour of solid dosage forms".
Plummer et al. (Dec. 2008) Clin Cancer Res 14(23):7917-7923, "Phase I Study of the Poly(ADP-Ribose) Polymerase Inhibitor, AG014699, in Combination with Temozolomide in Patients with Advanced Solid Tumors".
Search Report and Written Opinion dated Nov. 9, 2015 in PCT/US2015/045522.
Search Report dated Jan. 9, 2018 in SG application serial No. 11201700265V.
U.S. Department of Health and Human Services Food and Drug Administration Center for Drug Evaluation and Research (CDER), Jun. 2015, "Size, Shape, and Other Physical Attributes of Generic Tablets and Capsules Guidance for Industry".
Wilson et al. (2017) British Journal of Cancer 116:884-892, "A phase I study of intravenous and oral rucaparib in combination with chemotherapy in patients with advanced solid tumours".
Written Opinion dated Jan. 25, 2018 in SG application serial No. 11201700265V.

*Primary Examiner* — Jeffrey S Lundgren
*Assistant Examiner* — Stephanie K Springer
(74) *Attorney, Agent, or Firm* — Cooley LLP; Ivor R. Elrifi; Heidi A. Erlacher

(57) ABSTRACT

A tablet including high dosage of 8-fluoro-2-{4-[(methylamino)methyl]phenyl}-1,3,4,5-tetrahydro-6H-azepino[5,4,3-cd]indol-6-one camsylate salt has been disclosed.

11 Claims, 15 Drawing Sheets

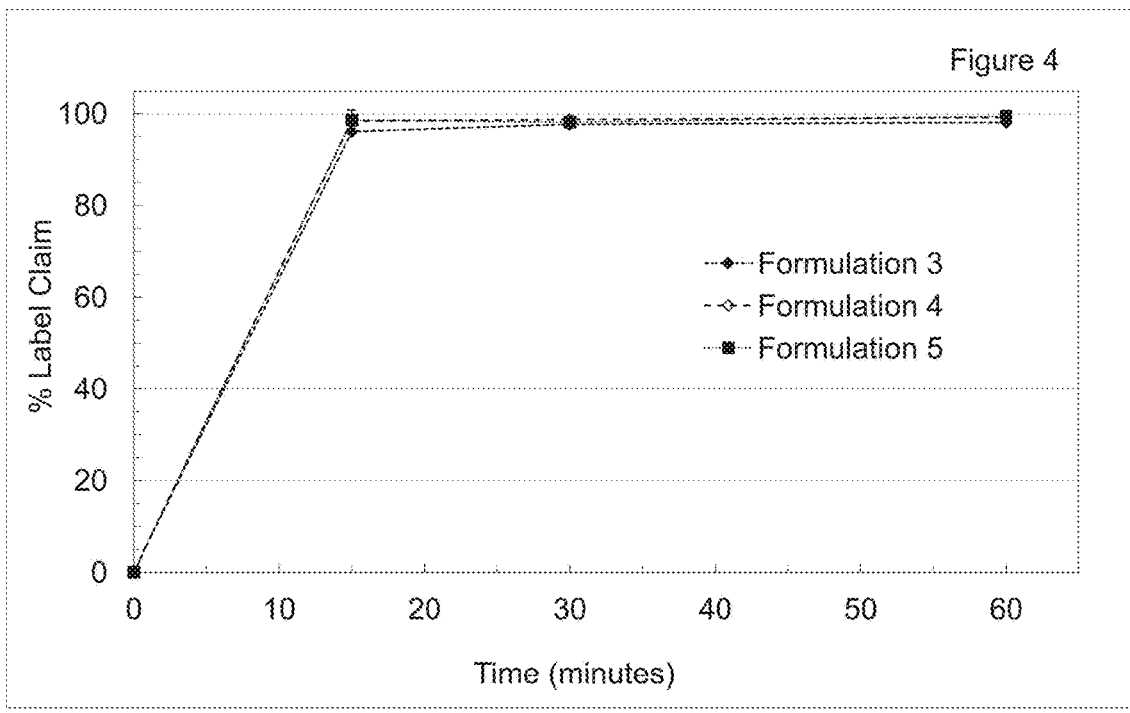

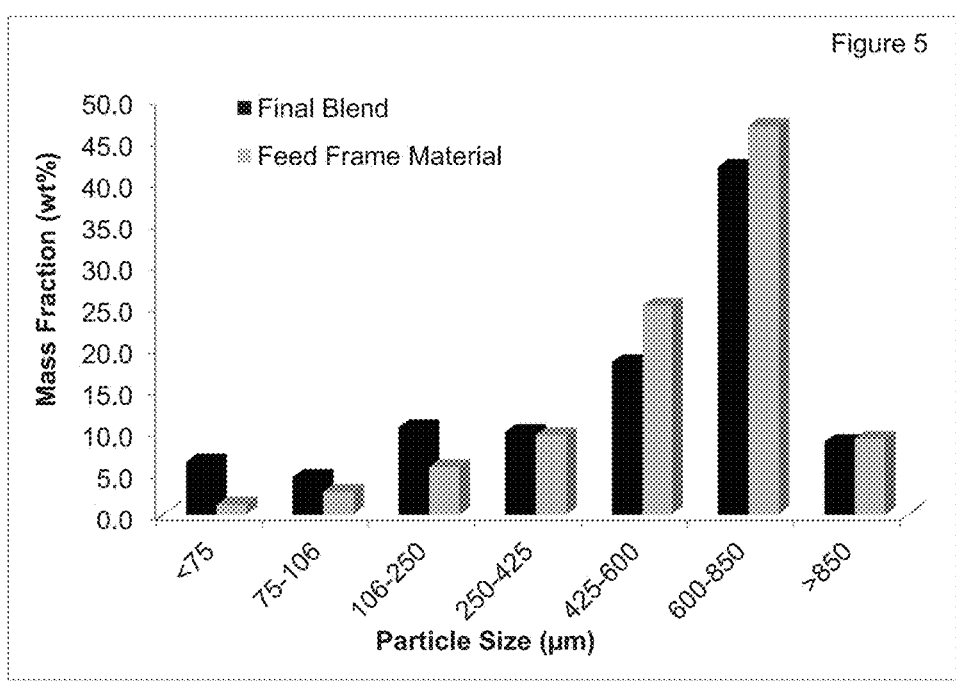

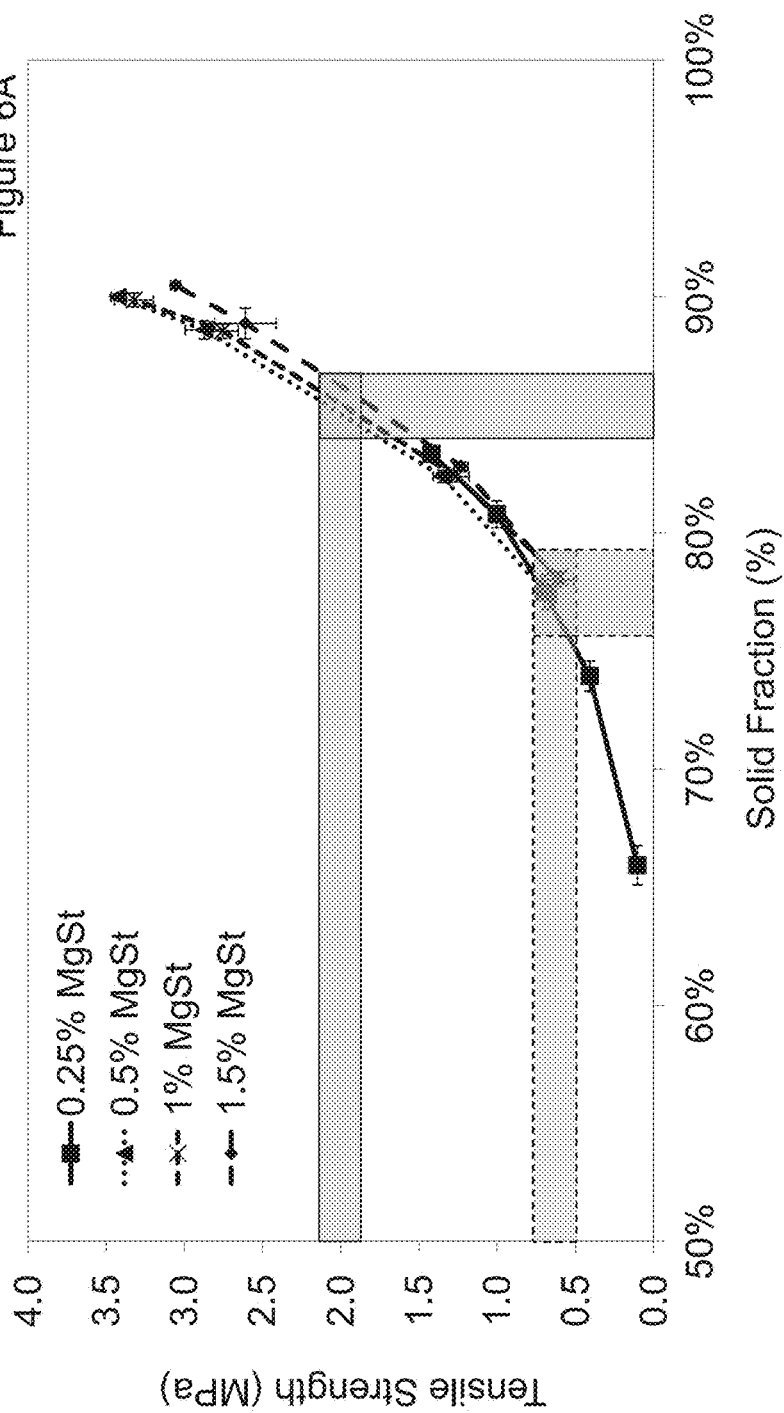

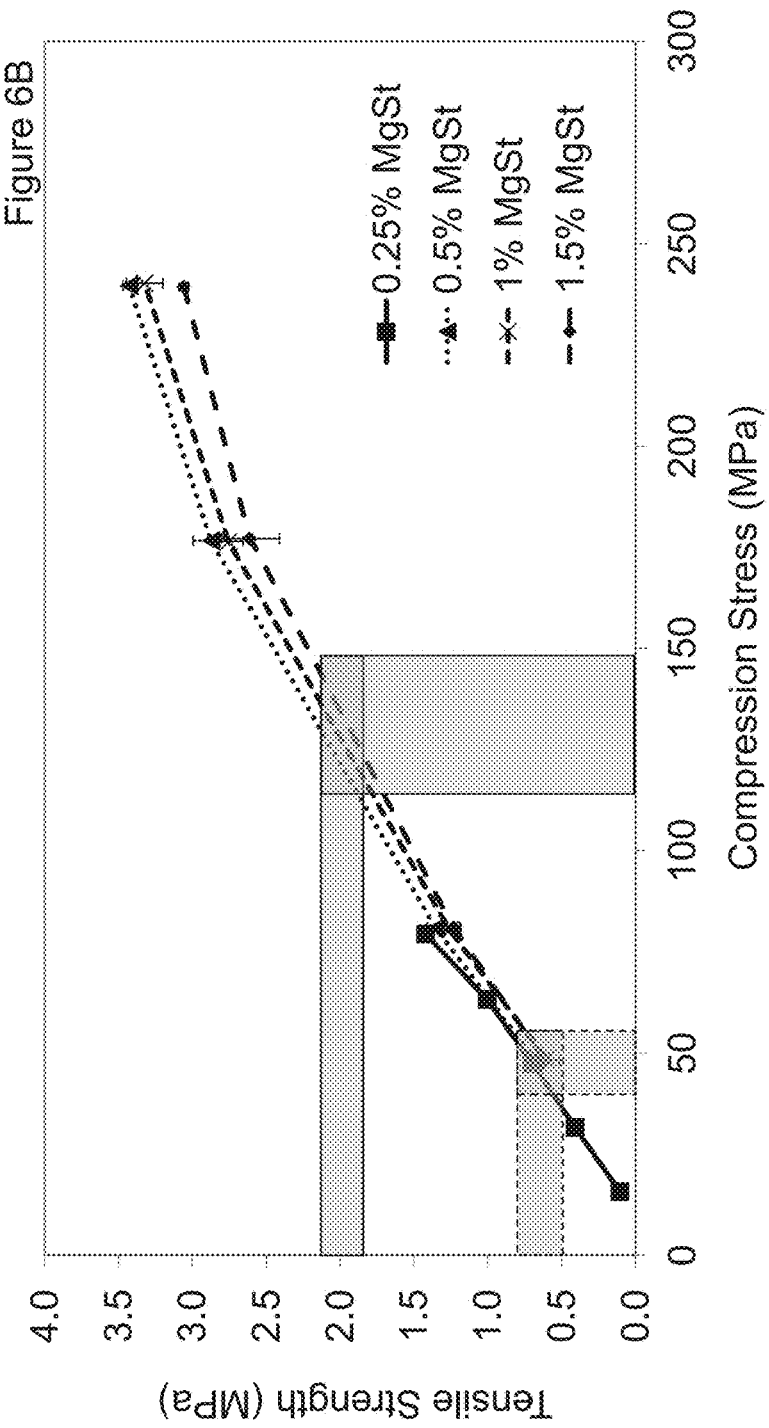

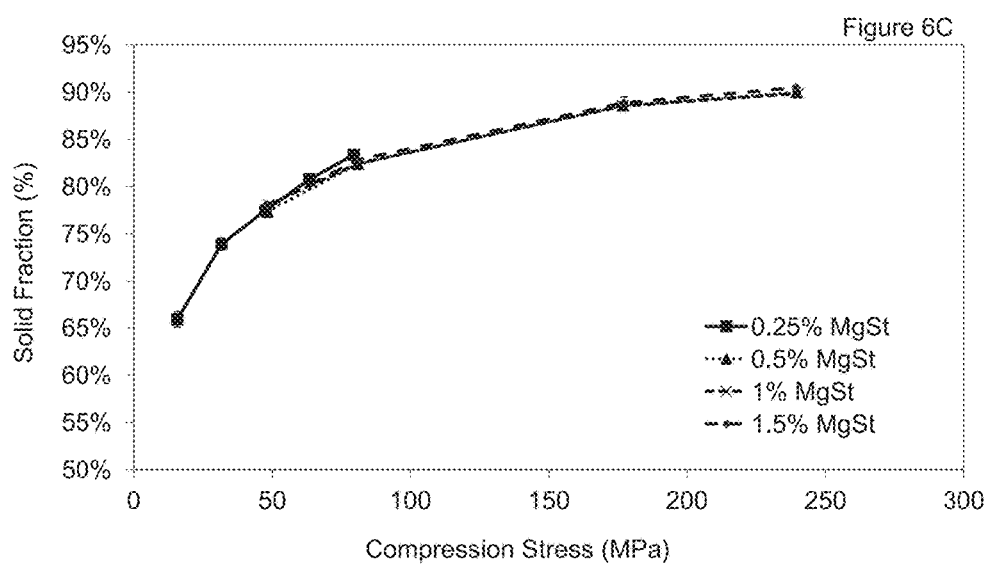

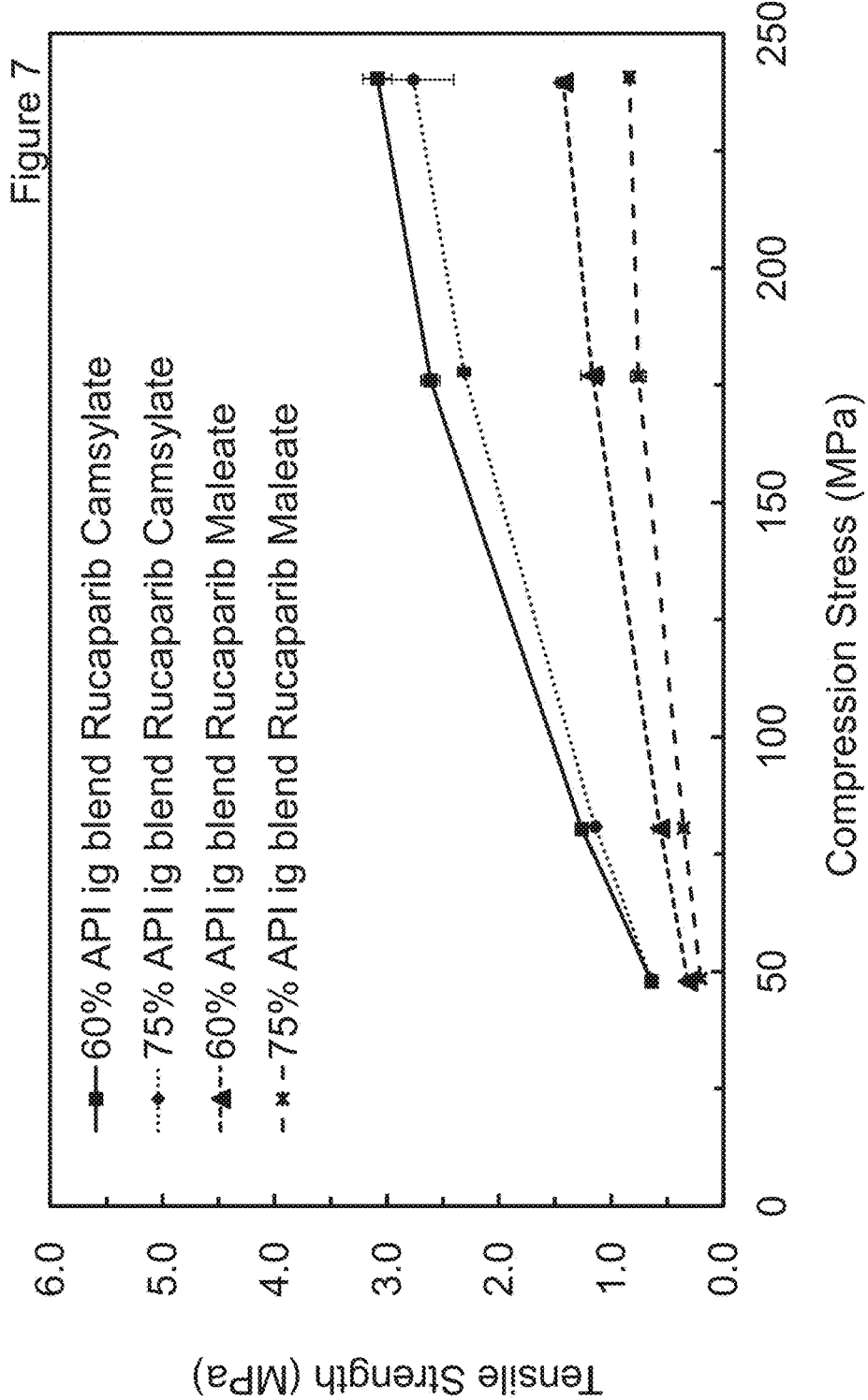

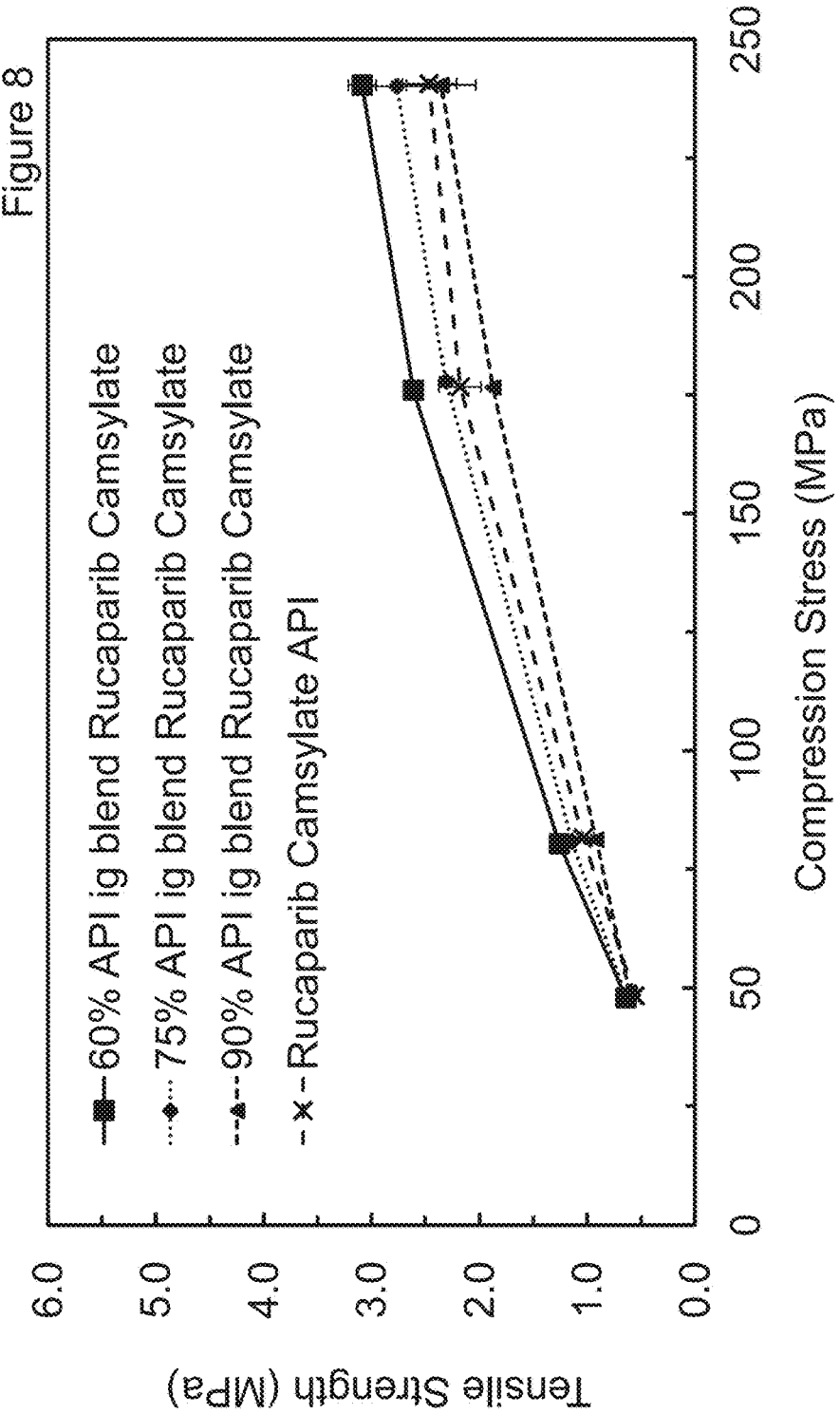

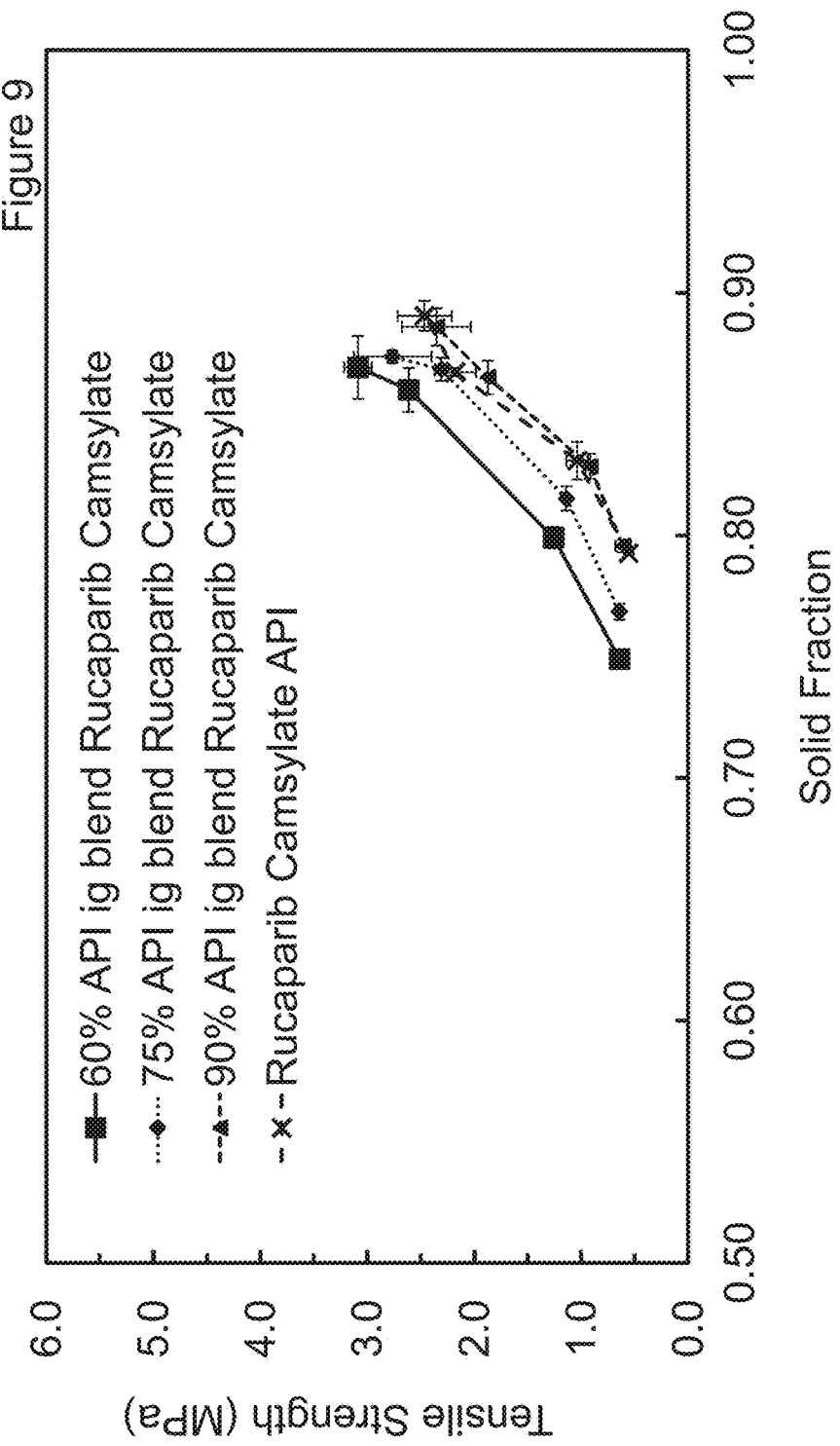

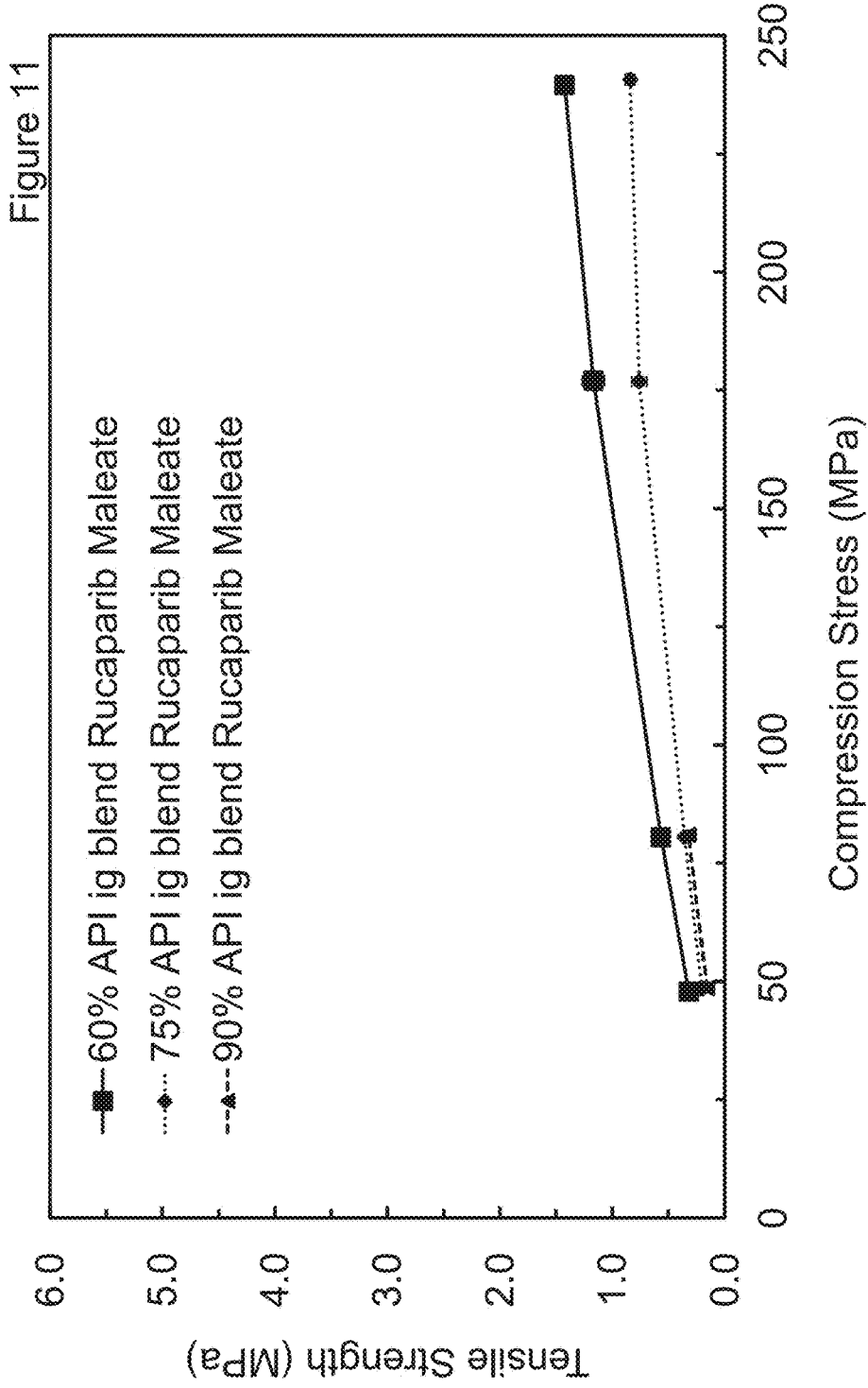

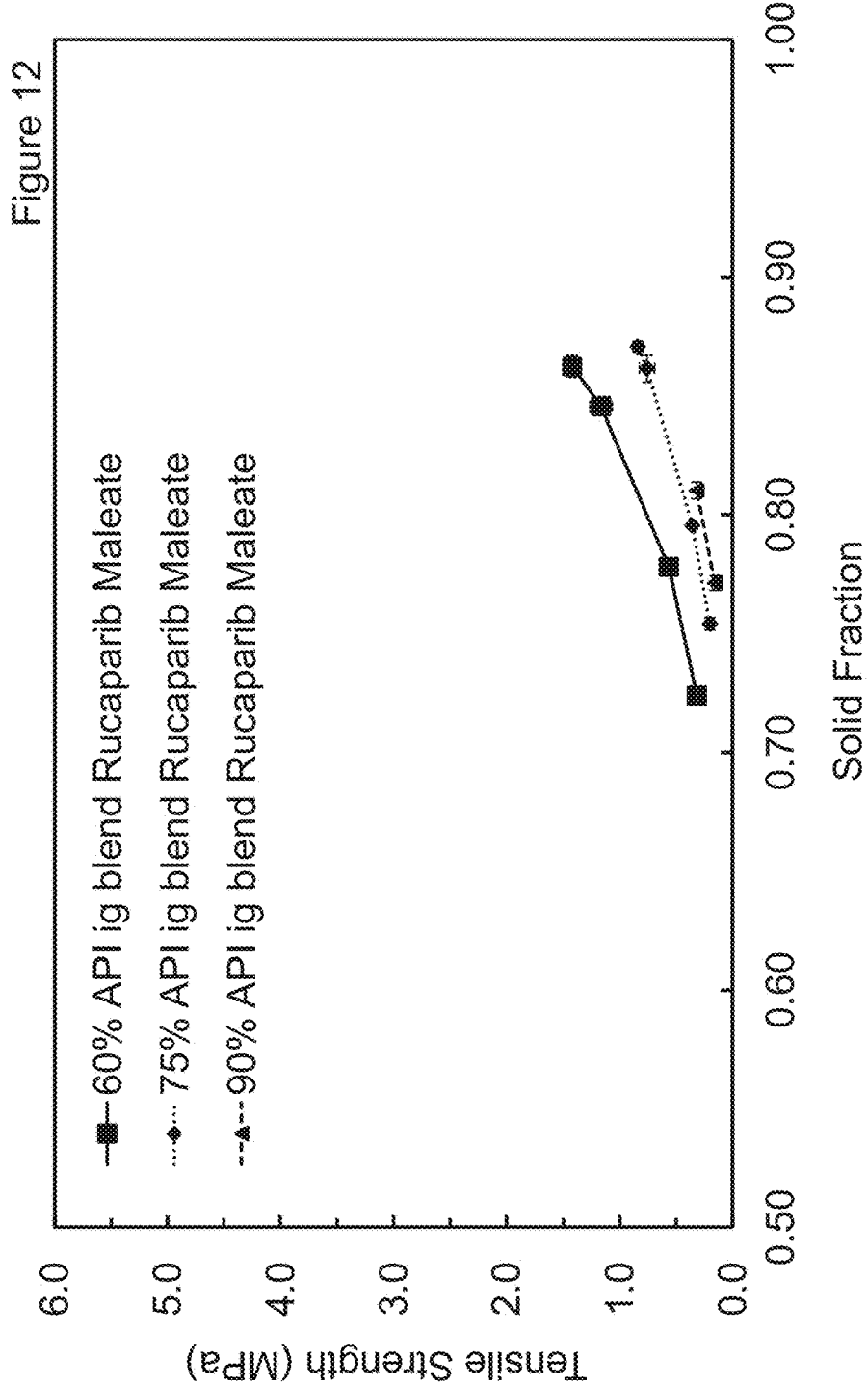

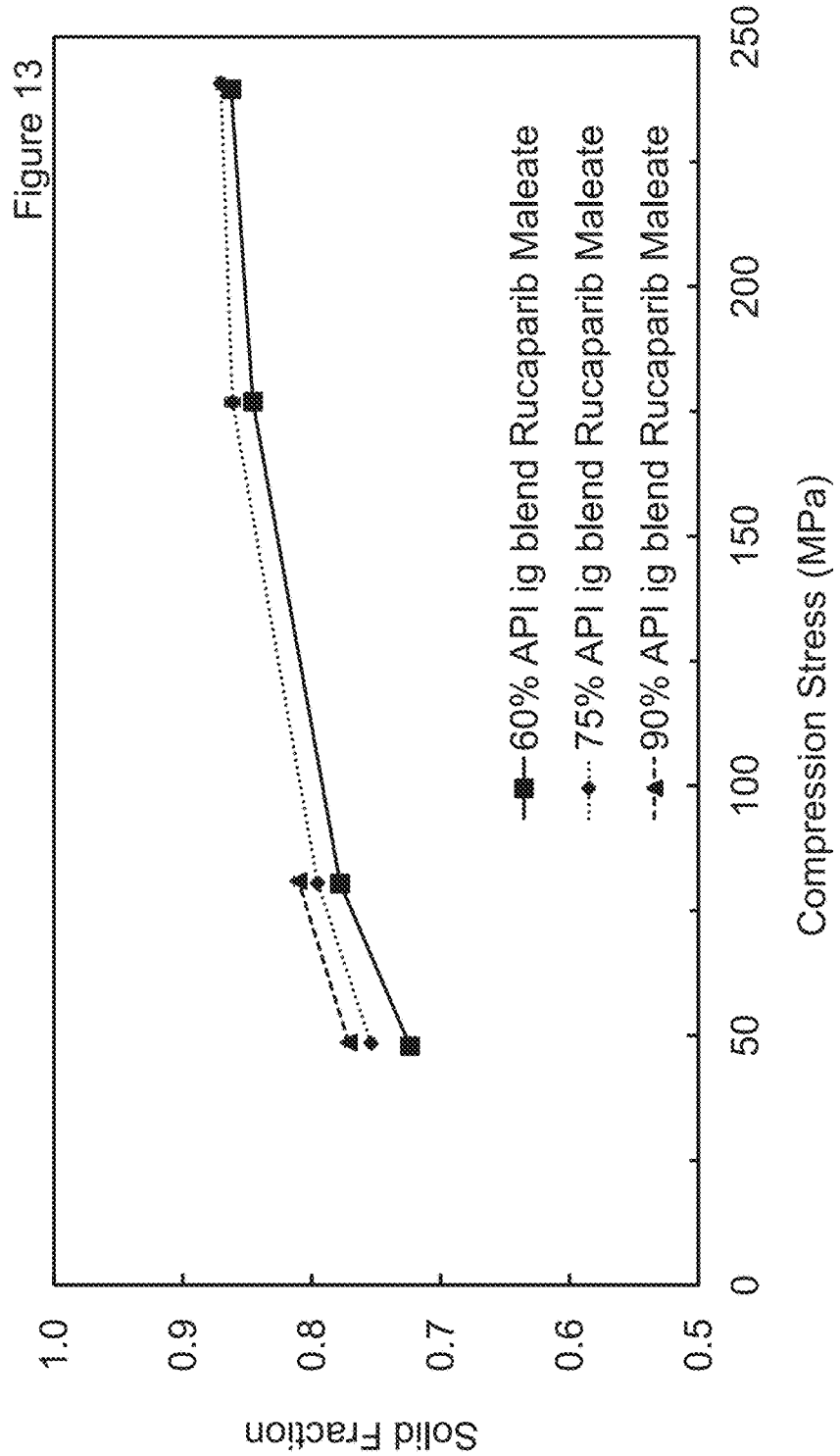

HIGH DOSAGE STRENGTH TABLETS OF RUCAPARIB

RELATED APPLICATIONS

This application is a divisional of U.S. application Ser. No. 14/828,065, filed Aug. 17, 2015, entitled "High Dosage Strength Tablets of Rucaparib." U.S. application Ser. No. 14/828,065 claims priority to U.S. provisional application Ser. No. 62/040,849, filed Aug. 22, 2014 and U.S. provisional application Ser. No. 62/101,739, filed Jan. 9, 2015. Each of the application referenced above are herein incorporated by reference in their entirety.

FIELD

The present disclosure relates, in general, to tablets of rucaparib, and more particularly, to high dosage strength tablets of rucaparib.

BACKGROUND

The compound 8-fluoro-2-{4-[(methylamino)methyl]phenyl}-1,3,4,5-tetrahydro-6H-azepino[5,4,3-cd]indol-6-one ("rucaparib") is a small molecule inhibitor of poly(ADP-ribose) polymerase (PARP).

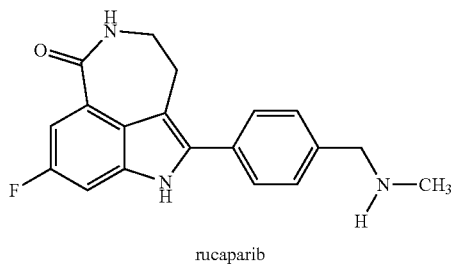 [SMILES: CNCc1ccc(-c2[nH]c3cc(F)cc4c3c2CCNC4=O)cc1]

rucaparib

Rucaparib, and methods of making it, are described, e.g., in U.S. Pat. Nos. 6,495,541 and 7,323,562. U.S. Pat. No. 6,495,541 describes salts of rucaparib in general, and solid dosage forms in general (col. 9, lines 7-61), with broad dose ranges expressed as mg/kg body weight (col. 26, lines 7-20). The issue of dose loading, i.e., percent drug content of the formulation, is not addressed. Certain salts and polymorphs of rucaparib are disclosed in U.S. Pat. Nos. 7,351,701, 7,351,530 and 7,268,126, and in U.S. Patent Application Publication No. 2004-0248879. U.S. Pat. Nos. 7,351,701 and 7,351,530 describe the use of the phosphate salt of rucaparib. They refer to all dosage forms generally, including tablets ('701 patent, col. 6, lines 48-57; '530 patent, col. 6, lines 30-38), though the only working example is of a liquid formulation of unspecified content. Again, the issue of dose loading is not addressed, and in fact it is stated that "only very low doses . . . are needed" ('701 patent, col. 6, lines 21-24; lines '530 patent, col. 6, lines 3-6). Published Application 2004-0248879 describes the phosphate and glucuronate salts of rucaparib, and solid dosage forms thereof generally (Paragraphs 0035-0036), with doses described in terms of mg/kg body weight (Paragraph 0036). No specific formulations are exemplified or described, and the issue of dose loading is not addressed.

U.S. Pat. No. 8,754,072 ("the '072 patent") discloses solid dosage forms of rucaparib maleate and rucaparib camsylate. The '072 patent states that of the pharmaceutically acceptable counter ions suitable for use with active ingredients, the maleate and camsylate salts of rucaparib were found to be less hygroscopic as compared to other salt forms (col. 11, lines 45-49), "making them particularly suitable in the preparation of solid dosage forms" (col. 11, lines 49-50). In addition, the maleate and camsylate salts of rucaparib were found to be more easily prepared and isolated than other salt forms (col. 11, lines 51-53). The '072 patent states very broadly that the compositions "will generally contain anywhere from about 0.001% by weight to about 99% by weight active ingredient," with preferred ranges of from about 0.01% to about 5% and about 0.01% to 2% (col. 36, lines 41-47). Embodiments containing 10%-25% active ingredient are also disclosed (col. 3, line 65-col. 4, line 9; col. 5, line 60-col. 6, line 4). The only working example of a formulation (Example 13) relates to a formulation comprising 17.18% of the camsylate salt. Thus, the '072 patent does not specifically address the issue of a high dose rucaparib formulation, and indeed, like the prior art discussed above, teaches that a lower dose loading (i.e., under 25%) is preferable.

Clinical development of oral rucaparib camsylate was initiated with tablets of lower strength (40 mg and 60 mg). As individual dose requirements increased a higher dosage strength of 120 mg was developed employing 32% drug loading and a dry granulation manufacturing process. Formulation modification relative to lower strengths was required to prepare 120 mg tablets, suggesting that drug loading significantly higher than 32% would be difficult to achieve with a dry granulation process.

Clinical studies of rucaparib indicated the need for a high unit dose (200 mg-800 mg) of active ingredient. For convenient oral administration, generally the tablet weight should not exceed 800 mg. As the number of tablets required per dose can lead to compliance issues, it would be desirable to find a formulation that could be commercially made that resulted in fewer tablets required per dose with the resultant expectation that there would be improved patient compliance.

Thus, there is a need for developing tablet dosage forms containing a rucaparib salt that 1) has suitable size in order to allow the patient to easily swallow the tablet, 2) has a high load of rucaparib in order to minimize the number of tablets required per dose, 3) has suitable properties with respect to the release of the rucaparib from the tablet, and 4) has the pharmaceutical behavior that leads to the desired effect. In some embodiments, the dosage form can be a capsule.

The overall physical properties and manufacturability of low drug loading formulations is determined predominantly by the inactive ingredients or excipients in the formulation. However, at high drug loading, the contribution of the physical properties of the active pharmaceutical ingredient ("API") to the manufacturability of a formulation becomes predominant. Not all APIs possess the necessary properties with respect to compressibility that are required in order to obtain a high load tablet using a dry granulation process.

Most small molecule API's, can be formulated in low dose forms because the physical properties of the excipients utilized in the formulations dominate the properties of the solid composition, rather than the physical properties of the API itself. As drug loading increases the physicochemical characteristics of the drug substance become increasing dominant in the tablet manufacturing process. It is common to include filler excipients in a single formulation that possess brittle characteristics and others that possess ductile/plastic characteristics. The combination of the brittle and plastic type materials in a given formulation are important to the "manufacturability" of that formulation. However, because API's can have a full spectrum of physical properties and are not selected based on these physical properties, it is not to be expected that a particular API would have the physical properties to favorably contribute to an overall formulation in terms of manufacturability and stability. In fact, it is not infrequent that it is the physical properties of the API that actually present the largest obstacle to creating a workable formulation. It is therefore surprising and unanticipated where it is found that an API can be formulated in a dry granulating manufacturing process with drug loads in excess of 45%. In fact, prior experience taught that it was likely not possible to create a formulation of rucaparib at a dose loading significantly exceeding 32%.

The ability to prepare rucaparib camsylate tablets at a drug loading in excess of 45% using a dry granulation process as described below is a surprising observation that is attributable to the unique physicochemical characteristics of the camsylate salt of rucaparib. In the current invention, no brittle filler excipients are necessary due to the unique and unexpected physicochemical characteristics of rucaparib camsylate.

As with hygroscopicity, and ease of manufacturing, the ability to form high dosage forms of an active ingredient may also be dependent on the specific salt form of the drug. However, hygroscopicity and ease of manufacturing at low dose loadings is not predictive of suitability for high dose formulations. This is demonstrated below, by the data presented herein showing that the maleate salt of rucaparib (showing favorable hygroscopicity and manufacturing properties in low dose formulations) cannot be formulated as a high dose form in a dry granulation manufacturing process.

In the present case, the inventors have surprisingly found that only one of the salt forms suitable for dry granulation manufacturing based on a constellation of physicochemical properties, such as hygroscopicity, brittle behavior and crystalline properties, would also have the appropriate physical properties for high dose formulations—i.e., the camsylate salt.

BRIEF SUMMARY

The invention is directed to high dosage strength tablets of rucaparib. In some embodiments, the tablet includes 45-90% w/w rucaparib camsylate. In some embodiments, the dry granulated tablet includes 45-90% w/w rucaparib camsylate. One such embodiment is a tablet containing at least 200 mg rucaparib. Another embodiment is a tablet containing at least 300 mg rucaparib.

In some embodiments, the method of treating a mammalian disease condition mediated by poly(ADP-ribose) polymerase activity, includes administering to a mammal in need thereof a therapeutically effective amount of the high dosage strength tablets of rucaparib. In some embodiments, a method of treating cancer in a mammal includes administering to the mammal a therapeutically effective amount of the high dosage strength tablets of rucaparib.

BRIEF DESCRIPTION OF THE DRAWINGS

FIG. 4 shows the dissolution results for the tablet formulations 3-5 in Table 1.

FIG. 5 shows particle size distributions of 300 mg final tablet blend and feedframe sample.

FIGS. 6A-C show compression profile versus magnesium stearate level evaluation.

FIG. 7 shows tabletability of rucaparib camsylate and maleate 60% and 75% loaded formulations.

FIG. 8 shows tabletability of intra granular rucaparib camsylate formulations.

FIG. 9 shows compactability of intra granular rucaparib camsylate formulations.

FIG. 11 shows tabletability of intra granular rucaparib maleate formulations.

FIG. 12 shows compactability of intra granular rucaparib maleate formulations.

FIG. 13 shows compressibility of intra granular rucaparib maleate formulations.

DETAILED DESCRIPTION OF CERTAIN EMBODIMENTS

Figure 1:
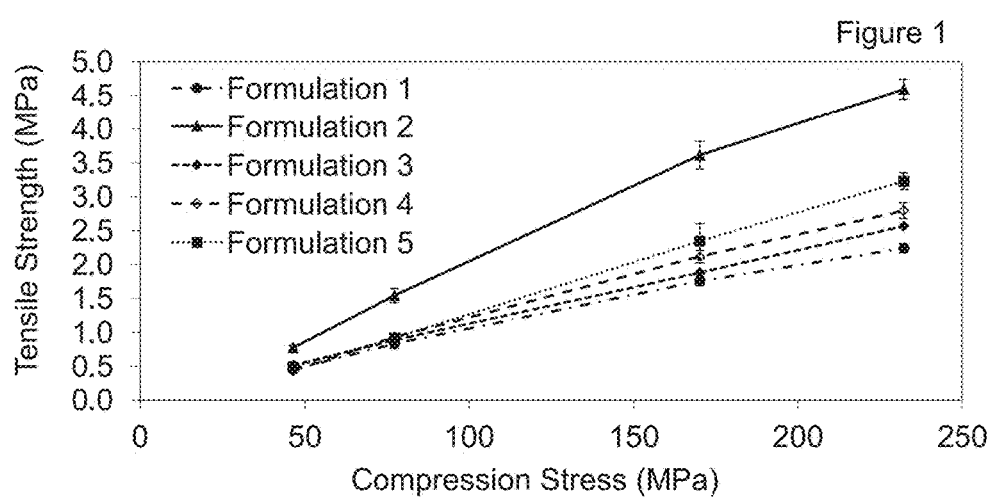
FIG. 1 shows the relationship of formulations 1-5 in Table 1 looking at the achievable tensile strength for a given compression stress.

While various aspects and features of certain embodiments have been summarized above, the following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present may be practiced without some of these specific details.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive.

Rucaparib camsylate salt possesses low hygroscopicity while retaining desirable physicochemical characteristics, e.g., polymorphic control and aqueous solubility, compared to other salts of rucaparib. The low hygroscopicity of the claimed salt is a commercially important property because it greatly facilitates the production of a solid dosage form of rucaparib for oral administration which is highly desirable to patients receiving rucaparib treatment.

Surprisingly, it was found that in addition to its low hygroscopicity rucaparib camsylate is a salt that has advantageous properties with respect to compressibility and that it is possible to manufacture tablets thereof with a load of 45% w/w or more. This means that the present invention provides tablets that may have such a high content of rucaparib that a necessary daily dose can be provided in one, two, or three tablets.

In some embodiments, the tablets contain 45-90% w/w rucaparib camsylate, such as, e.g., 50-90% w/w, 55-90% w/w, 60-90% w/w, 65-85% w/w, or 70-80% w/w rucaparib camsylate. In some embodiments, the tablets contain at least 300 mg rucaparib, such as, e.g., at least 350 mg, at least 400 mg, at least 450 mg, at least 500 mg, or at least 550 mg rucaparib. In some embodiments, the tablets contain at least 200 mg rucaparib, such as, e.g., at least 250 mg, at least 300 mg, or at least 350 mg rucaparib.

In order to obtain a desired pharmaceutical performance, the tablets must release rucaparib camsylate in a suitable time frame. In some embodiments, the tablet releases at least 95% w/w of rucaparib camsylate contained within the tablet within 30 min, when tested in 0.01N HCl according to USP II Paddles and at 75 rpm. In another embodiment, the tablet releases at least 95% w/w of rucaparib camsylate contained within the tablet within 15 min, when tested in 0.01N HCl according to USP II Paddles and at 75 rpm. In still another embodiment, the tablet releases at least 95% w/w of rucaparib camsylate contained within the tablet within 10 min, when tested in 0.01N HCl according to USP II Paddles and at 75 rpm.

The tablets may include one or more pharmaceutically acceptable excipients, carriers, or diluents/fillers. Surfactants, diluents, sweeteners, disintegrants, binders, lubricants, glidants, colorants, flavors, stabilizing agents, mixtures thereof and the like can be used. Fillers include both ductile filler and brittle fillers and include, but are not limited to, mannitol, sorbitol, xylitol, microcrystalline cellulose, silicified microcrystalline cellulose, hydroxypropyl methylcellulose, hydroxypropyl cellulose, pullulan and fast dissolving carbohydrates such as Pharmaburst™, mixtures thereof or the like. Ductile fillers yield and start to deform plastically after a critical stress. Ductile fillers often result in tablets of low porosity because the high degree of plastic deformation enables the particles to move very close to each other. Brittle fillers fragment into smaller units at a certain stress value. The fragmentation of brittle fillers results in an increase of smaller particles. Brittle fillers which undergo extensive fragmentation generally result in tablets of relatively high porosity because of the large number of bonding points that are created which prevent further volume reduction. Because rucaparib camsylate is fairly brittle, in some embodiments, a ductile excipient, for example microscrystalline cellulose is used as the main filler without a brittle filler.

Glidants are, but not limited to, silicon dioxide, colloidal silicon dioxide, calcium silicate, magnesium silicate, magnesium trisilicate, talc, starch, mixtures thereof or the like.

Lubricants are, but not limited to, calcium stearate, glyceryl monostearate, glyceryl behenate, glyceryl palmitostearate, hexagonal boron nitride, hydrogenated vegetable oil, light mineral oil, magnesium stearate, mineral oil, polyethylene glycol, poloxamer, sodium benzoate, sodium lauryl sulfate, sodium stearyl fumarate, stearic acid, talc, zinc stearate, mixtures thereof or the like.

Disintegrants are, but not limited to, sodium starch glycolate, sodium carboxymethyl cellulose, calcium carboxymethyl cellulose, croscarmellose sodium, crospovidone, chitosan, agar, alginic acid, calcium alginate, methyl cellulose, microcrystalline cellulose, powdered cellulose, lower alkyl-substituted hydroxypropyl cellulose, hydroxylpropyl starch, low-substituted hydroxypropylcellulose, polacrilin potassium, starch, pregelatinized starch, sodium alginate, magnesium aluminum silicate, polacrilin potassium, povidone, sodium starch glycolate, mixtures thereof or the like.

In some embodiments, the tablets contain 5-50% w/w filler, such as, e.g., 5-45% w/w, 5-40% w/w, 5-35% w/w, 5-30% w/w, 10-25% w/w, or 15-20% w/w filler. In some embodiments, the filler consists essentially of ductile filler(s). In some embodiments, the tablets contain 1-20% disintegrant, such as, e.g., 1-15% w/w, 1-10% w/w, 2-9% w/w, 3-8% w/w, 4-7% w/w, or 5-7% w/w disintegrant. In some embodiments, the tablets contain 0.20-2.5% w/w lubricant, such as, e.g., 0.2-2.0% w/w, 0.2-1.8% w/w, 0.2-1.5% w/w, or 0.25-1.5% w/w lubricant. In some embodiments, the tablets contain 0-1% w/w glidant, such as, e.g., 0.25-0.75% w/w, or 0.25-0.50% w/w glidant.

Dry granulation is a well-known pharmaceutical manufacturing process. In general, API is combined with excipients and lubricant and then compacted to form a mass. This mass typically is then comminuted or milled, then sieved to obtain the desired size of particle. The granular product is then compressed into tablets, filled into capsules or otherwise formed into a unitary dosage form in conventional fashion. In some embodiments, high dosage rucaparib tablets are produced by this process. In other embodiments, the granular product comprising high dosage rucaparib is filled into capsules or otherwise formed into a unitary dosage form.

Compaction into a mass is accomplished by conventional equipment. Typically, the blended API and excipients are passed through a roller compactor or chilsonator apparatus for compaction. However, other means for compacting, e.g., compaction into slugs (or "slugging"), the API/excipient blend optionally are used. This in turn is comminuted or milled, and then optionally sieved to produce the desired size granules.

A dry granulated composition comprising rucaparib camsylate is defined as the product of a dry granulation process. Dry granulated compositions include the direct product of dry granulation, i.e., dry granules per se, as well as products made from such granules including tablets, capsules, suppositories and other pharmaceutical dosage forms.

The tablet may be prepared by dry granulation comprising the steps of:

i) preparing a mixture containing rucaparib camsylate, ii) compacting the mixture obtained in step (i) by a compact roller to form a comprimate, iii) converting the comprimate obtained in step (ii) into a granulate, iv) optionally mixing the granulate obtained in step (iii) with a pharmaceutical excipient, and v) subjecting the granulate obtained in step (iii) or the mixture obtained in step (iv) to compression to obtain the tablet.

EXAMPLES

Example 1: Evaluation of Intra Granular Formulations

Intragranular means that these ingredients are found within the dry granule structure. Extragranular means the material is located externally to granule structure. Table 1 summarizes intra granular formulations that have been evaluated. Formulations 1 and 2 are considered best and worst case scenarios, with formulation 1 being pure 100% Rucaparib Camsylate API, and formulation 2 being used to manufacture the 120 mgA formulation. Formulations 3 and 4 were designed to look at different levels of ductile and brittle fillers, and formulation 5 was an increased tablet size to evaluate loading impact. All formulations 3-5 had the addition of colloidal silica dioxide (Cab-O-Sil) to aid in the flowability of the intra granular blends.

TABLE 1

| | Intragranular Formulations | | | | | |
|---|---|---|---|---|---|---|
| | Formulation | 1 | 2 | 3 | 4 | 5 |
| | Core Weight (mg) | N/A | 640 | 700 | 700 | 800 |
| | Dose (mgA) | N/A | 120 | 300 | 300 | 300 |
| Active (w/w) | Rucaparib Camsylate | 100.00% | 32.22% | 73.65% | 73.65% | 64.44% |
| Ductile Filler | Microcrystalline Cellulose PH101 | N/A | N/A | 13.23% | 18.86% | 19.69% |
| Ductile Filler | Microcrystalline Cellulose PH102 | N/A | 45.08% | N/A | N/A | N/A |
| Brittle Filler | Di-Calcium Phosphate | N/A | 19.16% | 5.63% | N/A | 8.37% |
| Disintegrant | Sodium Starch Glycolate | N/A | 2.81% | 6.00% | 6.00% | 6.00% |
| Glidant | Colloidal Silicon Dioxide | N/A | N/A | 0.50% | 0.50% | 0.50% |
| Lubricant | Magnesium stearate | N/A | 0.20% | 0.25% | 0.25% | 0.25% |

FIG. 1 shows the relationship of each formulation looking at the achievable tensile strength for a given compression stress. The maximum acceptable force considered within normal ranges on a rotary tablet press is approximately 250 MPa. A common target tensile strength for tablets is 2 MPa; such tablets generally have low friability, and are suitable for downstream handling and film coating. Thus, if a given formulation can be compressed to a tensile strength of 2 MPa at a compression stress of less than 250 MPa, it is considered to have acceptable compressibility. Formulations 3-5 had acceptable compressibility and were an improvement over API alone. While formulations with acceptable compressibility can be manufactured, it is preferred to maintain lower compression forces while still being able to achieve the target tensile strength as this provides more robustness to API, raw material and environmental variations and less wear on tableting equipment and tooling. Formulations 3-5 achieve this balance.

Figure 2:
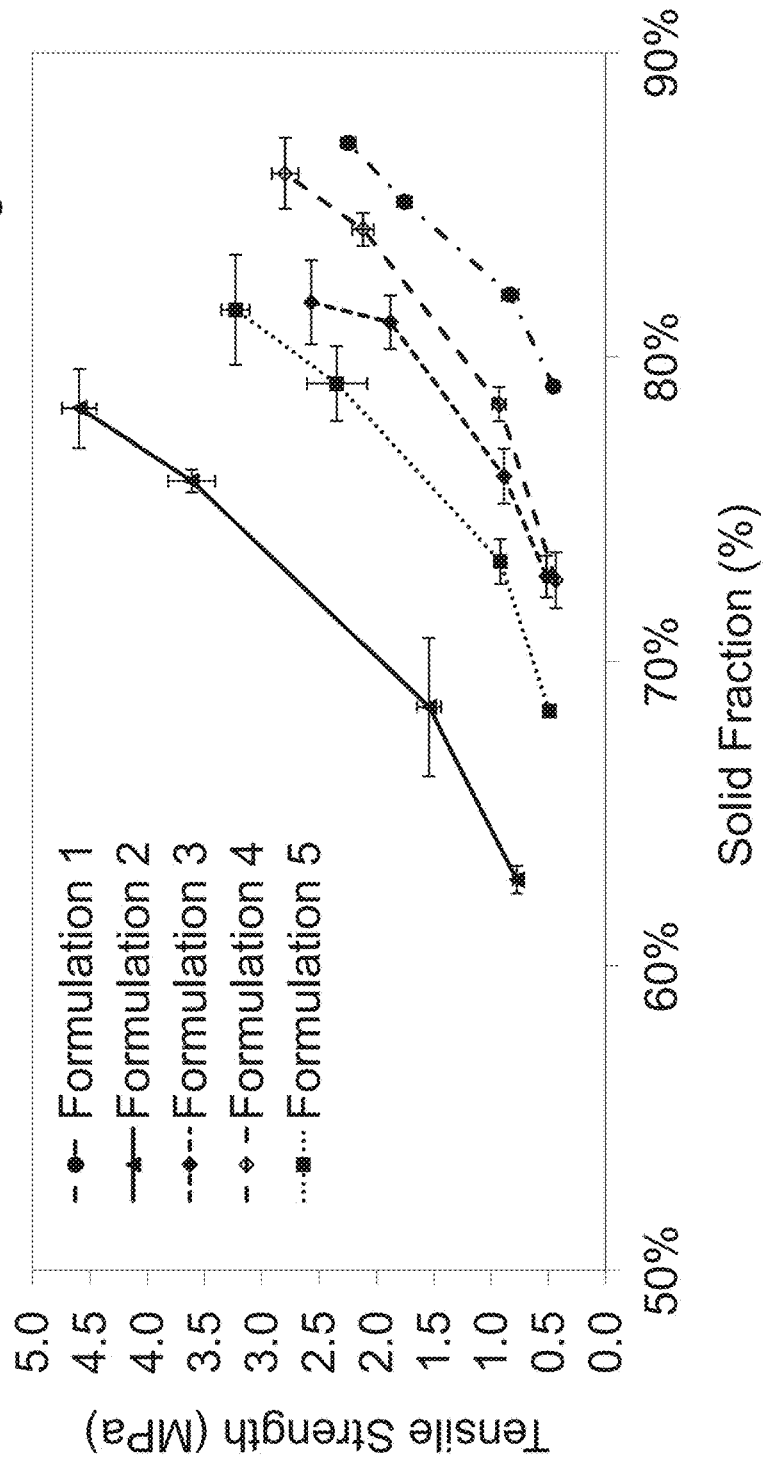
FIG. 2 shows tensile strength for a given solid faction of formulations 1-5 in Table 1.
Figure 3:
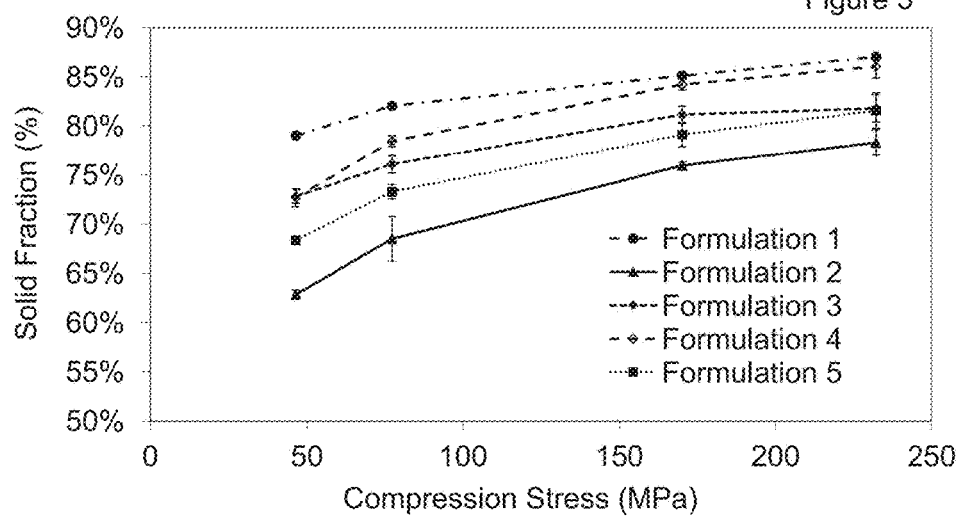
FIG. 3 shows tensile strength for a given compression stress of formulations 1-5 in Table 1.

FIGS. 2 and 3 provide information related to the solid fraction of formulation of rucaparib camsylate. It is important to ensure that tablets have efficient porosity so that fluid has the opportunity to effectively travel into the tablet and activate disintegration. All formulations tested have acceptable solid fractions for the target tensile strength and are within ranges of tablets containing API and excipients.

Example 2: Disintegration and Dissolution of High Dosage Formulations

Small scale batch of tablets from formulations 3-5 were manufactured and tested for disintegration and dissolution. The tablets were made using small scale slugging-based dry granulation and tablet compression techniques. Slugs were compacted at a relatively low tensile strength of approximately 0.3 MPa to minimize potential impact on final tablet compressibility, milled using a mortar/pestle and 20 mesh screen technique, and final blended with 0.5% Cab-O-Sil and 0.25% magnesium stearate added as extra granular excipients. Table 2 is a summary of the formulations that were manufactured into tablets and the corresponding tensile strength and hardness.

TABLE 2

Formulations Evaluated for correlating tensile strength and hardness

| | Formulation | | |
|---|---|---|---|
| | 3 | 4 | 5 |
| Core Weight (mg) | 700 | 700 | 800 |
| Dose (mgA) | 300 | 300 | 300 |

TABLE 2-continued

Formulations Evaluated for correlating tensile strength and hardness

| | | Formulation | | |
|---|---|---|---|---|
| | | 3 | 4 | 5 |
| Intra Granular Excipients | | | | |
| Active | Rucaparib Camsylate | 73.65% | 73.65% | 64.44% |
| Ductile Filler | Microcrystalline Cellulose PH101 | 13.23% | 18.86% | 19.69% |
| Ductile Filler | Microcrystalline Cellulose PH102 | N/A | N/A | N/A |
| Brittle Filler | Di-Calcium Phosphate | 5.63% | N/A | 8.37% |
| Disintegrant | Sodium Starch Glycolate | 6.00% | 6.00% | 6.00% |
| Glidant | Colloidal Silicon Dioxide | 0.50% | 0.50% | 0.50% |
| Lubricant | Magnesium stearate | 0.25% | 0.25% | 0.25% |
| Extra Granular Excipients | | | | |
| Glidant | Colloidal Silicon Dioxide | 0.50% | 0.50% | 0.50% |
| Lubricant | Magnesium stearate | 0.25% | 0.25% | 0.25% |
| Compression Data | | | | |
| Tensile Strength (MPa) | | 2.06 | 2.05 | 2.00 |
| Hardness (kP) | | 21.2 | 21.1 | 20.0 |

Table 3 shows disintegration results from a USP Disintegration apparatus with 0.01N HCl (pH=2.0) as the disintegration media. FIG. 4 shows the graphical dissolution results for the tablet formulations 3-5, performed in a USP Type II dissolution apparatus. The dissolution condition is: 0.01N HCl (pH=2.0), USP II Paddles, 75 rpm, Japanese Sinkers. Formulations 3-5 disintegrated and dissolved rapidly and completely. Table 4 shows the tabular dissolution results at 15 min, 30 min, and 60 min.

TABLE 3

Disintegration results for formulations 3-5 (USP Disintegration apparatus with 0.01N HCl (pH = 2.0) media).

| | Formulation 3 | Formulation 4 | Formulation 5 |
|---|---|---|---|
| Disintegration Time (sec) | 15 | 14 | 15 |
| Tensile Strength (MPa) | 2.06 | 2.05 | 2.00 |

TABLE 4

Dissolved percentage of formulations 3-5.

| Time (min) | Formulation 3 | Formulation 4 | Formulation 5 |
|---|---|---|---|
| | Average % Dose Dissolved | | |
| 15 | 96.10 | 98.40 | 98.60 |
| 30 | 97.65 | 98.71 | 98.14 |
| 60 | 98.08 | 99.14 | 99.39 |

Example 3: Particle Size Distributions of Final Tablet Blend and Feedframe Sample FIG. 5 shows particle size distributions of 300 mg final tablet blend of Formulation 4 and feed frame sample (at end of run). The particle size distribution is desirable for material handling and flow. The feed frame of the tablet press did not significantly change the particle size of the final blend during processing.

Example 4: Effect of Lubricant Level on Compressibility

FIGS. 6A-C show an intragranular magnesium stearate level evaluation. All compression profiles of intragranular blends made with varying levels of magnesium stearate have acceptable behavior. The boxes with solid lines represent the typical range of target tensile strengths for roller compaction and the correlating compression stress and solid fraction. The boxes with dashed lines represent the typical range of target tensile strengths for tableting and correlating compression stress and solid fraction. All intragranular blends with varying levels of magnesium stearate have acceptable achievable tensile strength values at less than 150 MPa compression stress.

Example 5: Tablet a Process

A 10-kg batch was made according to the formula in Table 5 using conditions in Tables 6-8. The blend was compacted by roller compaction on Gerteis Mini Pactor using the parameters listed in Table 6. Then, the compacted blend was granulated using the parameters listed in Table 7. Then, the granulated blend was tablet compressed on tablet press using the parameters listed in Table 8 to a target weight of about 700 mg.

TABLE 5

Composition of Tablet A
700 mg

| Ingredient | % of Blend | mg/tablet |
|---|---|---|
| Intragranular | | |
| Rucaparib Camsylate | 73.65% | 515.6 |
| Microcrystalline Cellulose PH 101 | 17.60% | 123.2 |
| Sodium Starch Glycolate | 6.00% | 42.0 |
| Colloidal Silicon Dioxide | 0.50% | 3.5 |
| Magnesium Stearate | 1.5% | 10.5 |

TABLE 5-continued

Composition of Tablet A
700 mg

| Ingredient | % of Blend | mg/tablet |
|---|---|---|
| (Extragranular) | | |
| Colloidal Silicon Dioxide | 0.50% | 3.5 |
| Magnesium Stearate | 0.25% | 1.8 |
| | 100% | 700.0 |

TABLE 6

| | |
|---|---|
| Roll Design | Smooth/Smooth |
| With Side Rim | Yes |
| Target Solid fraction | 0.70-0.75 |
| Tensile strength (MPa) | 0.2-0.4 |
| Compression Force (kN/cm) | 6 |
| Roll Speed (rpm) | 2 |
| Tamp/Feed Ratio (%) | 160-200 |
| Gap Width (mm) | 2 |

TABLE 7

| | |
|---|---|
| Rotor Type | Pocket |
| Screen Size | 1.0 |
| Mill Gap Setting | 1 mm |
| Mill Gap Measured | 1.3 mm |
| Rotor Direction | CW 240, CCW 300 |
| Rotor rpm | 60 |
| Gap Control Activated | yes |
| Torque Control OFF | OFF |

TABLE 8

| | |
|---|---|
| Tooling | 0.3183 × 0.6367 M.O. |
| Tablet Weight | 700 mg |
| Target Hardness | 23kP |
| Tensile strength (MPa) | ~2.05 |
| Compression Force (kN) | 22 |
| Feeder Speed (rpm) | 15-20 |
| Turret Speed (RPM) | 20 |

Example 6: Evaluating Tablet Compressibility Properties of Rucaparib Camsylate and Maleate Salts Studies with low dose rucaparib tablets have shown that rucaparib camsylate and rucaparib maleate possess a constellation of physicochemical properties that may be useful in solid dosage forms. However, previous work suggested that dose loading at higher than 32% API would be difficult, if not impossible, to achieve. This example is an evaluation of rucaparib camsylate and maleate salts for compressibility properties with respect to dry granulation processing for the manufacture of a high API-loading tablet. The objective was to identify a salt form of rucaparib with properties suitable for high dose formats for dry granulation tablet compression.

The most relevant and broadly accepted approach to assessing compression evaluation of different formulations (and different API salts) is by measuring the interrelationships of compression stress, solid fraction, and tensile strength using a compaction simulator. These parameters are related to each other in a set of relationships referred to as compressibility, tabletability, and compactability profiles (i.e., CTC Profiles) (Tye, Sun, Amidon, J. Pharm. Sci, 94: 465-472, (2005)).

Focus was on the intra granular blend rather than the final blend because nearly all of the lead formulation is processed through dry granulation; only a small portion is extra granular. Additionally, the extra granular lubrication step at small scale is not representative of downstream pilot or commercial processing and risks masking intrinsic compressibility properties. For the provided lot of each salt form, formulations were evaluated at 100%, 90%, 75%, and 60% of the final tablet formulation (this correlates to 100%, 90.68%, 75.57%, and 60.45% intra granular components).

Table 10 summarizes the formulations evaluated. Both salt forms of rucaparib were evaluated at various loadings of the API, including one formulation for each whereby pure API was tested.

CTC profiles for each API and formulation were determined by compressing (Texture Technologies model TA.XT Plus Texture Analyzer), in triplicate, ¼" round flat-faced 100 mg compacts using a linear sawtooth strain profile at 5 mm/sec velocity to four pre-programmed peak forces encompassing roller compaction and tableting compression stress ranges (e.g., up to ~240 MPa). The compacts were then evaluated for physical dimensions, weight, and hardness. From these data and measured true density (Micromeritics Accypyc 1340 helium pynchnometer), the compression stress, tensile strength and solid fraction values were calculated and the respective CTC profiles generated.

The maximum acceptable compression stress considered within normal ranges of a commercial rotary tablet press is approximately 250 MPa. Similarly, a typical target tensile strength for tablets is 2 MPa; such tablets generally have low friability, and are suitable for downstream handling and film coating. Thus, if a given formulation can be compressed to a tensile strength of 2 MPa at a compression stress of less than 250 MPa, it is considered to have acceptable compressibility.

The most direct comparison of the salt compressibility would be pure API without excipients. However, the pure maleate salt compacts were not able to be formed. Attempts to create compacts at very high forces—and even at a reduced, 90%, loading—resulted in compacts that flaked apart, capped and therefore were not able to be assessed for tensile strength or other compaction parameters. This result was the first indication the maleate API is not amendable to compression in higher loading tablet formulations. Surprisingly, the camsylate API formed good compacts that show good tableting properties for all formulations evaluated, including pure API.

Tabletability is the most direct relationship of the CTC profiles to illustrate capability to form tablets on rotary tablet presses. FIG. 7 and Table 9 show the tabletability (compression stress verses tensile strength) comparison of the two most relevant formulations for the projected 300 mg (non-salt basis) tablet strengths –60 and 75% API loading.

TABLE 9

Tabular Data

| Salt Form | Drug Load | Compression Stress (MPa) | Compression Stress (Std Dev) | Tensile Strength (MPa) | Tensile Strength (Std Dev) |
|---|---|---|---|---|---|
| Camsylate | 60% | 47.9 | 0.1 | 0.6 | 0.0 |
|  |  | 80.3 | 0.6 | 1.3 | 0.0 |
|  |  | 176.0 | 0.1 | 2.6 | 0.1 |
|  |  | 240.4 | 1.1 | 3.1 | 0.1 |

TABLE 9-continued

Tabular Data

| Salt Form | Drug Load | Compression Stress (MPa) | Compression Stress (Std Dev) | Tensile Strength (MPa) | Tensile Strength (Std Dev) |
|---|---|---|---|---|---|
| Camsylate | 75% | 48.3 | 0.5 | 0.6 | 0.0 |
|  |  | 80.8 | 0.1 | 1.1 | 0.0 |
|  |  | 177.8 | 0.8 | 2.3 | 0.1 |
|  |  | 240.1 | 0.9 | 2.8 | 0.4 |
| Maleate | 60% | 47.9 | 0.2 | 0.3 | 0.0 |
|  |  | 80.4 | 0.4 | 0.6 | 0.1 |
|  |  | 177.0 | 0.5 | 1.2 | 0.1 |
|  |  | 239.5 | 1.1 | 1.4 | 0.1 |
| Maleate | 75% | 48.5 | 0.4 | 0.2 | 0.0 |
|  |  | 80.5 | 0.2 | 0.4 | 0.0 |
|  |  | 176.8 | 0.9 | 0.8 | 0.1 |
|  |  | 240.7 | 1.1 | 0.8 | 0.0 |

The camsylate salt formulations show superior tensile strength values, amendable to tablet compression, at much lower compression forces than the maleate salt. Indeed, the maleate salt formulations do not achieve the target tensile strength of 2 MPa even at 250 MPa; furthermore, the curve's asymptotic appearing plateau at >200 MPa suggests acceptable tensile strength tablets may not be achievable at all, even at extreme compression forces. Stated differently, the tabletability of the maleate salt is approximately 2-2.5× lower than the camsylate salt, and falls below the acceptable threshold for tableting. Thus, substantially lower loaded maleate salt formulations would be required for dry granulation tableting, when compared to the camsylate salt.

Since all of the 60-100% loaded camsylate formulations show achievable tensile strength of at least 2.0 MPa at modest compression stresses (see FIG. 8), a general conclusion can be made that all are acceptable from a tabletability standpoint. Conversely, none of the 60-100% maleate salt formulations achieved 2.0 MPa tensile strength (FIGS. 7 and 11).

Figure 10:
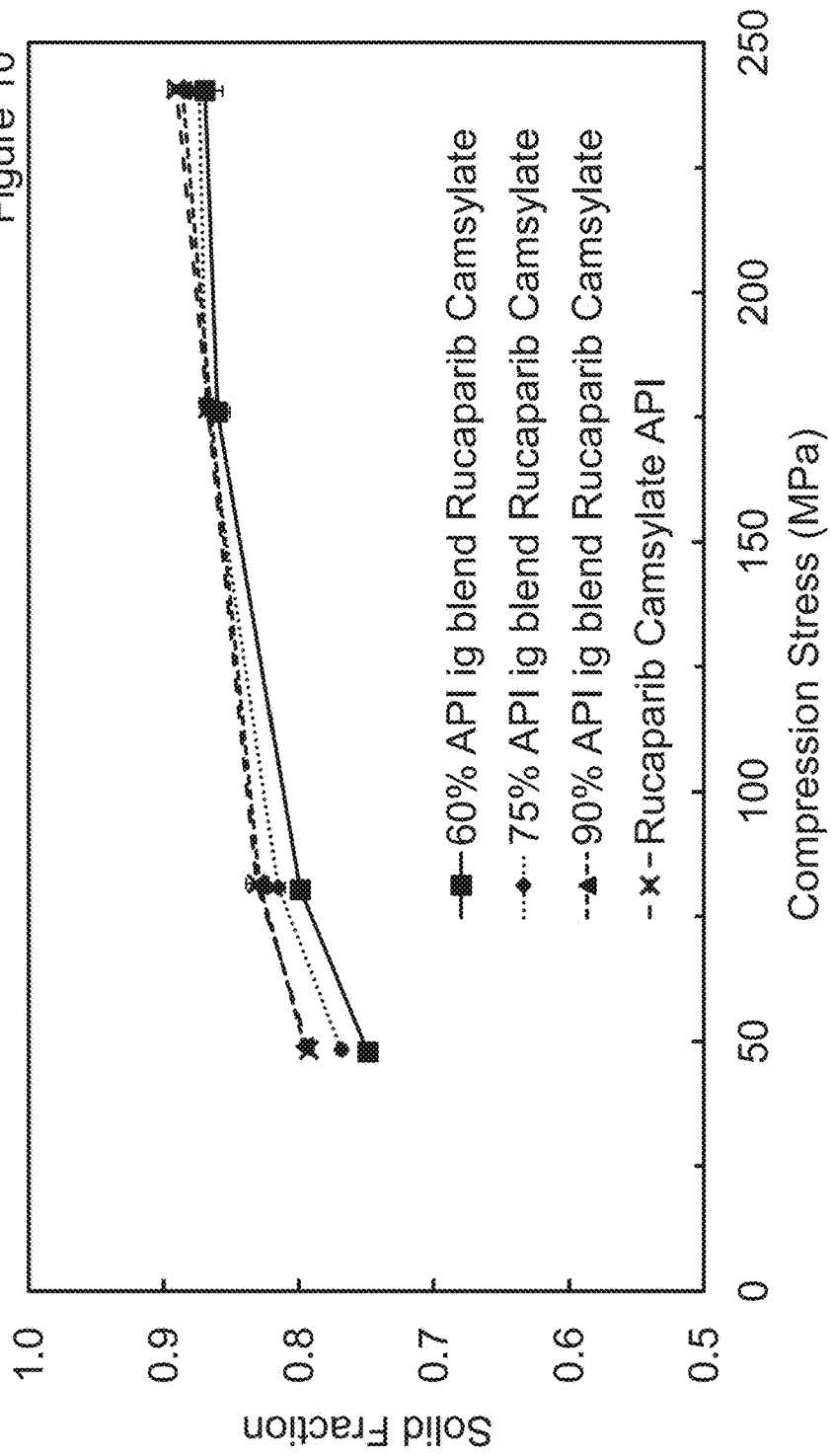
FIG. 10 shows compressibility of intra granular rucaparib camsylate formulations.

The data shown in FIGS. 8-10 are the CTC profiles for the 4 formulations that were analyzed with the camsylate salt. Similarly, the data shown in FIGS. 11-13 are the CTC profiles for the 3 formulations that were capable of being analyzed for the maleate salt. The pure maleate salt was not amendable to analysis based on inability to form intact compacts at 90% and 100% API formulations.

The CTC profiles generated show that the camsylate salt evaluated is much more amendable to dry granulation and tablet compression processes. Additionally, the maleate salt compressibility is inferior to the camsylate salt such that maleate drug loading would need to decrease from the target of >70% to estimated <50% to obtain tablets with sufficient strength for downstream coating, packaging, and/or shipping processes.

Last, it is notable that the CTC profiles to camsylate API loading over 60-100% is not highly sensitive to API loading. Thus, compressibility should not be limiting for very high loading (high dose:tablet size ratio) tablets. Rather, the upper limit would likely be other quality or processing attributes such as disintegration, dissolution, powder flow or sticking, making tablet strengths of rucaparib camsylate greater than 300 mg possible.

TABLE 10

Initial Intra Granular Formulations Evaluated for Rucaparib Salt Forms

|  | Formulation | 1 | 2 | 3 | 4 | 5 | 6 | 7 | 8 |
|---|---|---|---|---|---|---|---|---|---|
| Active | Rucaparib Camsylate | 60.45% | 75.57% | 90.68% | 100.0% | NA | NA | NA | NA |
| Active | Rucaparib Maleate | NA | NA | NA | NA | 60.45% | 75.57% | 90.68% | 100.0% |
| Ductile Filler | Microcrystalline cellulose (Avicel PH101) | 31.49% | 16.37% | 1.26% | 0.00% | 31.49% | 16.37% | 1.26% | 0.00% |
| Disintegrant | Sodium Starch Glycolate (Explotab) | 6.00% | 6.00% | 6.00% | 0.00% | 6.00% | 6.00% | 6.00% | 0.00% |
| Glidant | Colloidal Silica Dioxide (CabOSil MSP) | 0.50% | 0.50% | 0.50% | 0.00% | 0.50% | 0.50% | 0.50% | 0.00% |
| Lubricant | Magnesium stearate | 1.50% | 1.50% | 1.50% | 0.00% | 1.50% | 1.50% | 1.50% | 0.00% |

What is claimed is:

1. A method of treating cancer in a mammal, the method comprising administering to the mammal a therapeutically effective amount of a tablet comprising 45-90% w/w of an active pharmaceutical ingredient compound 8-fluoro-2-{4-[(methylamino)methyl]phenyl}-1,3,4,5-tetrahydro-6H-azepino[5,4,3-cd]indol-6-one camsylate.

2. The method according to claim 1, wherein the active pharmaceutical ingredient is included in the range of 50-90%.

3. The method according to claim 1, wherein the active pharmaceutical ingredient is included in the range of 55-90%.

4. The method according to claim 1, wherein the active pharmaceutical ingredient is included in the range of 60-90%.

5. The method according to claim 1, wherein the active pharmaceutical ingredient is included in the range of 65-85%.

6. The method according to claim 1, wherein the active pharmaceutical ingredient is included in the range of 70-80%.

7. The method according to claim 1, wherein the tablet includes 200 mg or more of 8-fluoro-2-{4-[(methylamino)methyl]phenyl}-1,3,4,5-tetrahydro-6H-azepino[5,4,3-cd]indol-6-one.

8. The method according to claim 1, wherein the tablet includes 250 mg or more of 8-fluoro-2-{4-[(methylamino)methyl]phenyl}-1,3,4,5-tetrahydro-6H-azepino[5,4,3-cd]indol-6-one.

9. The method according to claim 1, wherein the tablet includes 300 mg or more of 8-fluoro-2-{4-[(methylamino)methyl]phenyl}-1,3,4,5-tetrahydro-6H-azepino[5,4,3-cd]indol-6-one.

10. The method according to claim 1, wherein the mammal is a human being.

11. A method of treating cancer in a mammal, the method comprising administering to the mammal a therapeutically effective amount of a dry granulated tablet comprising 45-90% w/w of an active pharmaceutical ingredient compound 8-fluoro-2-{4-[(methylamino)methyl]phenyl}-1,3,4,5-tetrahydro-6H-azepino[5,4,3-cd]indol-6-one camsylate, wherein the tablet includes 200 mg or more of 8-fluoro-2-{4-[(methylamino)methyl]phenyl}-1,3,4,5-tetrahydro-6H-azepino[5,4,3-cd]indol-6-one.

* * * * *